United States Patent
Kuroiwa et al.

(10) Patent No.: US 11,850,101 B2
(45) Date of Patent: Dec. 26, 2023

(54) MEDICAL IMAGE DIAGNOSTIC APPARATUS, MEDICAL IMAGE PROCESSING APPARATUS, AND MEDICAL IMAGE PROCESSING METHOD

(71) Applicant: Canon Medical Systems Corporation, Otawara (JP)

(72) Inventors: Koji Kuroiwa, Fuchu (JP); Shogo Fukuda, Kawasaki (JP); Takeshi Fukasawa, Nasushiobara (JP); Fumio Mochizuki, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 1202 days.

(21) Appl. No.: 16/026,184

(22) Filed: Jul. 3, 2018

(65) Prior Publication Data
US 2019/0008482 A1  Jan. 10, 2019

(30) Foreign Application Priority Data

Jul. 5, 2017  (JP) ................ 2017-131831
Jul. 2, 2018  (JP) ................ 2018-125780

(51) Int. Cl.
*A61B 8/00* (2006.01)
*A61B 8/08* (2006.01)
*A61B 8/06* (2006.01)
*A61B 8/12* (2006.01)

(52) U.S. Cl.
CPC ............. *A61B 8/5246* (2013.01); *A61B 8/06* (2013.01); *A61B 8/08* (2013.01); *A61B 8/0883* (2013.01); *A61B 8/12* (2013.01); *A61B 8/463* (2013.01); *A61B 8/469* (2013.01); *A61B 8/483* (2013.01);

(Continued)

(58) Field of Classification Search
CPC .................................................. A61B 8/5246
See application file for complete search history.

(56) References Cited

U.S. PATENT DOCUMENTS

| | | | | |
|---|---|---|---|---|
| 6,480,732 B1 * | 11/2002 | Tanaka | .................... | G06T 15/08 |
| | | | | 382/128 |
| 2002/0087061 A1 * | 7/2002 | Lifshitz | .................... | A61B 8/00 |
| | | | | 600/407 |

FOREIGN PATENT DOCUMENTS

| | | |
|---|---|---|
| JP | 2006-218210 | 8/2006 |
| JP | 2007-44231 | 2/2007 |
| JP | 2009-291295 | 12/2009 |

(Continued)

OTHER PUBLICATIONS

Office Action dated Apr. 19, 2022 in Japanese Application No. 2018-125780.

*Primary Examiner* — Joseph M Santos Rodriguez
(74) *Attorney, Agent, or Firm* — Oblon, McClelland, Maier & Neustadt, L.L.P.

(57) ABSTRACT

According to one embodiment, a medical image diagnostic apparatus includes processing circuitry. The processing circuitry configured to acquire first volume data and second volume data relating to a subject, set a first region of interest for the first volume data, set a second region of interest for the second volume data independently from setting of the first region of interest, perform a cropping process on the first volume data and the second volume data based on information representing the first region of interest and the second region of interest, and generate display image data based on the first volume data and the second volume data that have been subjected to the cropping process.

22 Claims, 5 Drawing Sheets

(52) U.S. Cl.
CPC ............ *A61B 8/488* (2013.01); *A61B 8/5207* (2013.01); *A61B 8/4411* (2013.01)

(56) References Cited

FOREIGN PATENT DOCUMENTS

| | | |
|---|---|---|
| JP | 2010-099195 | 5/2010 |
| JP | 2012-66027 | 4/2012 |

* cited by examiner

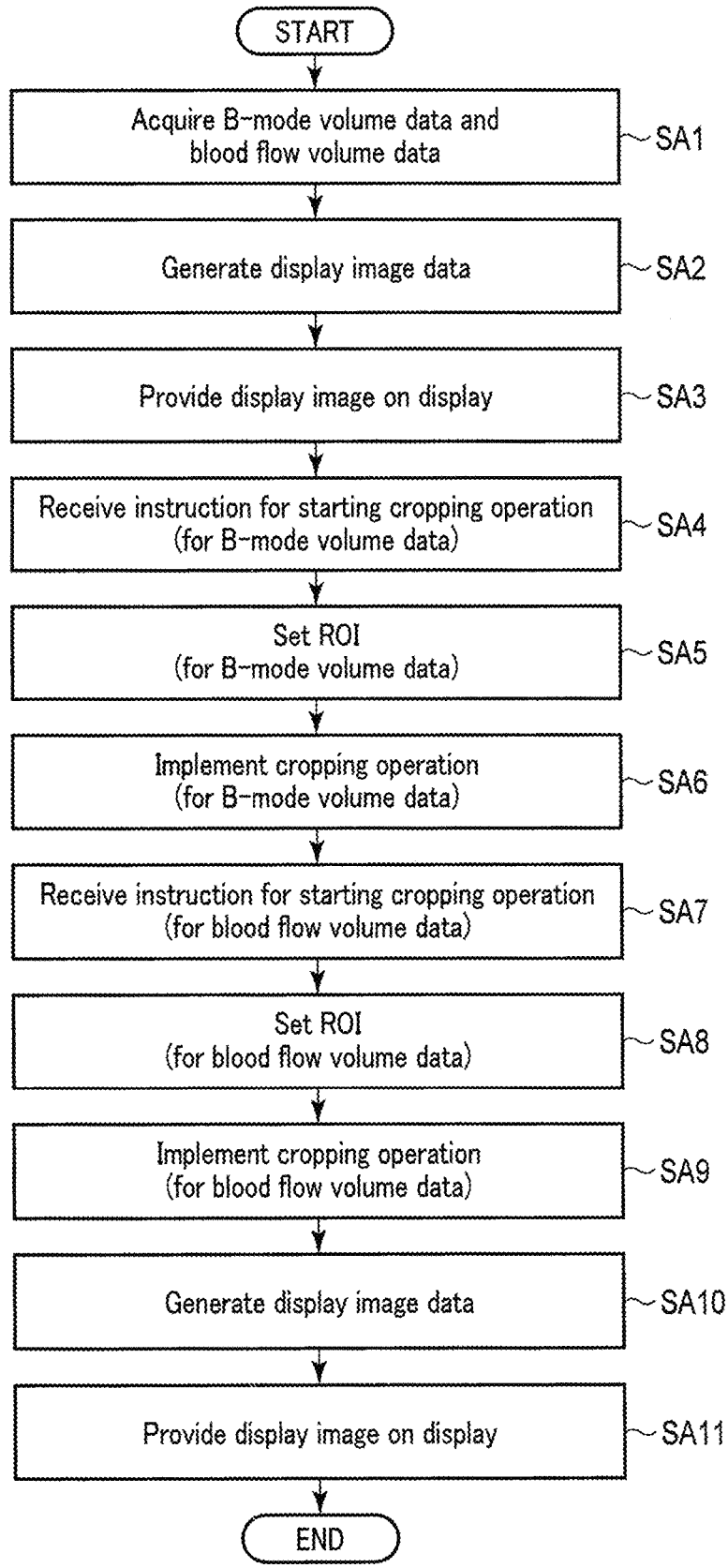
F I G. 2

MEDICAL IMAGE DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application is based upon and claims the benefit of priority from the prior Japanese Patent Application No. 2017-131831, filed Jul. 5, 2017 and No. 2018-125780, filed Jul. 2, 2018, the entire contents of both which are incorporated herein by reference.

FIELD

Embodiments described herein relate generally to a medical image diagnostic apparatus, medical image processing apparatus, and medical image processing method.

BACKGROUND

An ultrasound diagnostic apparatus is designed to acquire volume data (3D image data) of a B-mode image that represents morphological information and volume data of a blood flow (color Doppler) image that represents blood flow information, using a Matrix TransEsophageal Echocardiography (TEE) probe or the like. By observing a subject in a three-dimensional manner in the ultrasonic diagnosis using the acquired sets of volume data, multiple two-dimensional images that are to be examined can be examined at a time. The analysis of, for example, the volume data of a B-mode image allows an operator to visually and quantitatively ascertain the morphological information of the region to be examined, in comparison with two-dimensional ultrasonic image data. The analysis of the volume data of a blood flow image allows for three-dimensional visualization of regurgitation from, for example, a cardiac valve.

The ultrasound diagnostic apparatus is provided with a cropping function, with which the volume data of any three-dimensional region can be cut and displayed out of a certain set of volume data. This cropping function is implemented when cross-sectional image data of a cross-sectional image is cut away from volume data that is displayed by superimposing the volume data of the B-mode image and the volume data of a blood flow image. For such a display, there is a need for the cropping function that allows for extraction of different regions for the volume data of the B-mode image and for the volume data of the blood flow image; for example, the extraction of the region in the vicinity of the cardiac valve may be needed for the volume data of the B-mode image, while the extraction of the region from the vicinity of the cardiac valve to the position where the regurgitation can be identified may be needed for the volume data of the blood flow image.

The conventional cropping function, however, allows for extraction of only the same region, based on the region of interest commonly designated for the volume data of the B-mode image and the volume data of the blood flow image. This means that the volume data of the B-mode image and the volume data of the blood flow image cannot be independently extracted. For this reason, if the volume data obtained by superimposing the volume data of the B-mode image and the volume data of the blood flow image is subjected to the cropping process, the need for displaying only the blood flow information for the region expanding from the outer and vicinal area of the cardiac valve to the regurgitation identifiable position of the cardiac valve cannot be satisfied.

BRIEF DESCRIPTION OF THE DRAWINGS

FIG. 2 is a flowchart of the operations of control circuitry when the ultrasound diagnostic apparatus according to the present embodiment performs a cropping process onto volume data.

DETAILED DESCRIPTION

Figure 1:
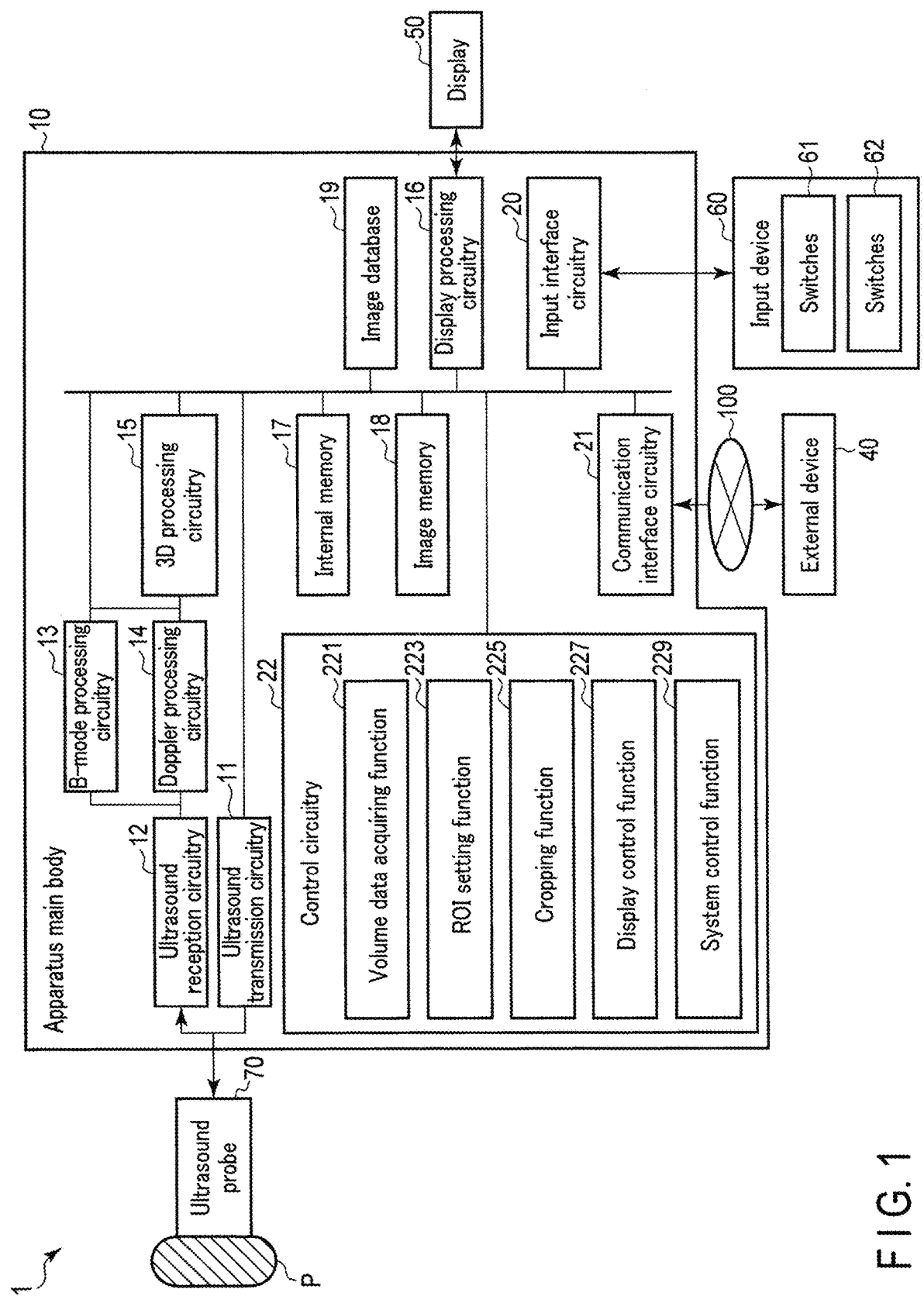
FIG. 1 is a diagram showing the structure of an ultrasound diagnostic apparatus according to the present embodiment.

In general, according to one embodiment, a medical image diagnostic apparatus includes processing circuitry. The processing circuitry configured to acquire first volume data and second volume data relating to a subject, set a first region of interest for the first volume data, set a second region of interest for the second volume data independently from setting of the first region of interest, perform a cropping process on the first volume data and the second volume data based on information representing the first region of interest and the second region of interest, and generate display image data based on the first volume data and the second volume data that have been subjected to the cropping process.

The present embodiment will be explained below, by referring to the drawings.

An ultrasound diagnostic apparatus 1 according to the present embodiment will be explained by referring to the block diagram of FIG. 1.

As illustrated in FIG. 1, the ultrasound diagnostic apparatus 1 comprises an apparatus main body 10, an ultrasound probe 70, a display 50, and an input device 60. The apparatus main body 10 is coupled to an external device 40 via a network 100. The apparatus main body 10 is also coupled to the display 50 and input device 60.

The ultrasound probe 70 includes a plurality of piezoelectric transducers, a matching layer arranged on the piezoelectric transducers, and a backing member that prevents ultrasound waves from propagating backward from the piezoelectric transducers. The ultrasound probe 70 is coupled to the apparatus main body 10 in a detachable manner. The piezoelectric transducers generate ultrasonic waves in accordance with a drive signal supplied from ultrasound transmission circuitry 11 of the apparatus main body 10. The ultrasound probe 70 may be provided with buttons that are to be pressed for an offset process, or at the time of freezing an ultrasonic image for example.

When ultrasonic waves are transmitted from the ultrasound probe 70 to a subject P, the transmitted ultrasonic waves are sequentially reflected by the surface of the subject P where the value of the acoustic impedance is discontinuous, and are received as reflection wave signals (echo signals) by the piezoelectric transducers of the ultrasound probe 70. The amplitude of a received reflection wave signal depends on the difference in values of the acoustic impedance on the discontinuous surface from which the ultrasonic wave is reflected. If the transmitted ultrasonic pulse is reflected from the surface of, for example, a moving blood stream or cardiac wall, the frequency of the resultant reflection wave signal is shifted due to the Doppler effect, with the shift dependent on the velocity component with respect to the ultrasound transmission direction of the moving object. The ultrasound probe 70 receives the reflection wave signal from the subject P, and converts it into an electrical signal. According to the present embodiment, the ultrasound probe 70 is designed to acquire volume data (three-dimensional image data). In particular, the ultrasound probe 70 may be a two-dimensional array probe in which a plurality of piezoelectric transducers are arranged in a two-dimensional matrix, or a mechanical four-dimensional probe that can implement an ultrasonic scan by tilting the aligned piezoelectric transducers in the direction orthogonal to the direction of the alignment.

The apparatus main body 10 illustrated in FIG. 1 generates an ultrasonic image based on the reflection wave signal received by the ultrasound probe 70. As illustrated in FIG. 1, the apparatus main body 10 includes ultrasound transmission circuitry 11, ultrasound reception circuitry 12, B-mode processing circuitry 13, Doppler processing circuitry 14, 3D processing circuitry 15, display processing circuitry 16, an internal memory 17, an image memory 18 (cinememory), an image database 19, input interface circuitry 20, communication interface circuitry 21, and control circuitry 22.

The ultrasound transmission circuitry 11 is a processor that supplies a drive signal to the ultrasound probe 70. The ultrasound transmission circuitry 11 may be realized by trigger generation circuitry, delay circuitry, pulser circuitry, and the like. The trigger generation circuitry repeats the generation of rate pulses for formation of transmission ultrasound waves at a predetermined rate frequency under the control of the control circuitry 22. The delay circuitry provides each rate pulse generated by the trigger generation circuitry with a delay time for each piezoelectric transducer so that the ultrasound waves generated by the ultrasound probe 70 can be converged into a beam and its transmission directivity can be determined. The pulser circuitry applies a drive signal (drive pulse) to the ultrasound probe 70 at the timing based on the rate pulse under the control of the control circuitry 22. The delay circuit changes the delay time that is to be provided to each rate pulse so that the direction of the transmission from the piezoelectric transducer surface can be adjusted as needed.

The ultrasound reception circuitry 12 is a processor that performs various processes onto the reflection wave signals received by the ultrasound probe 70 and thereby generates reception signals. The ultrasound reception circuitry 12 may be realized by amplifier circuitry, an analog-digital converter, reception delay circuitry, an adder, and the like. The amplifier circuitry amplifies the reflection wave signal received by the ultrasound probe 70 for respective channels, and thereby performs gain correction processing. The A/D converter converts the gain-corrected reflection wave signal into a digital signal. The reception delay circuitry provides the digital signal with a delay time that is used for determining the reception directivity. The adder adds up digital signals to which the delay time is provided. As a result of the adding process by the adder, a reception signal having an enhanced reflection component from a direction corresponding to the reception directivity is generated.

The B-mode processing circuitry 13 is configured to generate B-mode data based on the reception signals received from the ultrasound reception circuitry 12. The B-mode processing circuitry 13 performs an envelope wave detection process and logarithmic amplification process onto the reception signals received from the ultrasound reception circuitry 12, and thereby generates data (B-mode data) that indicates signal intensities by levels of brightness. The generated B-mode data is stored in a raw data memory (not shown) as B-mode raw data obtained from a two-dimensional ultrasonic scan line.

The Doppler processing circuitry 14 generates a Doppler wave and Doppler data based on the reception signals received from the ultrasound reception circuitry 12. The Doppler processing circuitry 14 extracts blood flow signals from the reception signals, and generates a Doppler waveform from the extracted blood flow signals. The Doppler processing circuitry further generates data (Doppler data) obtained by extracting, from the blood flow signals, information on the average velocity, distribution, and power at multiple points. The generated Doppler data is stored in a raw data memory (not shown) as Doppler raw data obtained from a two-dimensional ultrasonic scan line.

The 3D processing circuitry 15 is configured to generate various volume data, based on the data generated by the B-mode processing circuitry 13 and the Doppler processing circuitry 14.

For example, the three-dimensional processing circuitry 15 performs, onto the B-mode data stored in the raw data memory, a raw-voxel conversion including an interpolating process by factoring in spatial positional information, and thereby generates B-mode volume data representing mode information. The 3D processing circuitry 15 also performs, on the Doppler data that is stored in the raw data memory, a raw-voxel conversion that includes an interpolation process by factoring in spatial positional information, and thereby generates blood flow volume data representing blood flow information. The B-mode volume data and blood flow volume data are constituted by voxels in a desired range. Each voxel of the B-mode volume data has a specific pixel value (voxel value) assigned in accordance with the signal intensity of the reflection wave signal. Each voxel of the blood flow volume data has a specific pixel value assigned in accordance with the direction and velocity of the blood stream.

The 3D processing circuitry 15 further performs a rendering process onto the various types of volume data that have been generated, and thereby generates rendering image data. The 3D processing circuitry 15 also performs a multiplanar reconstruction (MPR) process onto the various volume data, and thereby generates MPR image data that represents a certain cross-sectional image (MPR image) of the volume data. The 3D processing circuitry 15 performs a curved multiplanar reconstruction (MPR) process onto the various volume data, and thereby generates curved cross-sectional image data that represents a curved cross-sectional image of the volume data. The 3D processing circuitry 15 combines the generated B-mode volume data and blood flow volume data, and thereby generates composite volume data. A combining method may be realized by adding, to the pixel value of each voxel of the B-mode volume data, the pixel value of the corresponding voxel of the blood flow volume data multiplied by a specific weighting factor.

The display processing circuitry 16 displays various images on the display 50. The display processing circuitry 16 generates ultrasonic image data as a display image by coordinate conversion processing or the like. The coordinate conversion processing is to convert, for example, a signal sequence of an ultrasonic scan line including by B-mode data and Doppler data, into video signals that are a scan line signal sequence of a common video format typified, for example, by a television format. The generated ultrasonic image data is converted, for example, into a format compliant with the digital imaging and communication in medicine (DICOM), and is stored, for example, in the image database 19.

The display processing circuitry 16 generates B-mode image data based on the B-mode raw data stored in the raw data memory. The B-mode image data has pixel values (brightness values) that reflect, for example, the characteristics of the ultrasound probe, such as acoustic wave convergence, and acoustic field characteristics of ultrasound beams (e.g., transmission/reception beams). For example, the B-mode image data exhibits a relatively higher brightness, in and around the portion in which the ultrasound wave is in focus, than in the portion in which the ultrasound is out of focus in the scanned area. The display processing circuitry 16 displays the generated B-mode image data onto the display 50 as an ultrasonic image.

The display processing circuitry 16 generates Doppler image data representing an average speed image, a distribution image, a power image and the like, based on the Doppler raw data stored in the raw data memory. The display processing circuitry 16 displays the generated Doppler image data on the display 50 as an ultrasonic image.

The display processing circuitry 16 performs various processes including corrections to the dynamic range, brightness, contrast, and γ curve, as well as an RGB conversion, onto various image data generated at the three-dimensional processing circuitry 15, and thereby converts the image data to a video signal. The display processing circuitry 16 displays the video signal onto the display 50 as an ultrasonic image.

The display processing circuitry 16 may generate a user interface (Graphical User Interface, or GUI) with which the operator (for example, surgeon) can input various instructions via the input interface circuitry 20, and may display the GUI onto the display 50. As the display 50, a CRT display, a liquid crystal display, an organic EL display, an LED display, a plasma display, or any other display known in the relevant technical field may be adopted as appropriate. The display 50 is provided, for example, with a notification function.

The internal memory 17 includes a processor-readable storage medium such as a magnetic or optical storage medium or a semiconductor memory. The internal memory 17 stores therein a control program for realizing ultrasound transmission and reception, a control program for performing image processing, and a control program for performing display processing, and the like. The internal memory 17 also stores control programs for realizing various functions according to the present embodiment. Furthermore, the internal memory 17 stores data groups such as diagnostic information (including patient IDs and medical opinions), diagnostic protocols, a body mark generation program, and a conversion table that presets the range of visualization color data for respective diagnostic sites. The internal memory 17 may store anatomical charts, such as an atlas, of the structure of organs of a living body.

The internal memory 17 further stores volume data and rendering image data generated by the 3D processing circuitry 15, in accordance with the storing operation input through the input interface circuitry 20. The volume data and rendering image data generated by the 3D processing circuitry 15 may be stored in the internal memory 17 in accordance with the storing operation input through the input interface circuitry 20, together with the operating order and operating time. The internal memory 17 may be configured to transmit the stored data to an external device via the communication interface circuitry 21.

The image memory 18 includes a processor-readable storage medium such as a magnetic or optical storage medium or a semiconductor memory. The image memory 18 stores the image data corresponding to a plurality of frames immediately before the freezing operation that is input through the input interface circuitry 20. The image data stored in the image memory 18 may be sequentially displayed (cine-displayed).

The image database 19 stores therein the image data transmitted from the external device 40. For example, the image database 19 may obtain from the external device 40 the history image data of the same patient obtained from past medical examinations, and may store it therein. The history image data includes ultrasonic image data, computed tomography (CT) image data, magnetic resonance (MR) image data, positron emission tomography/computed tomography (PET-CT) image data, PET-MR image data, and x-ray image data. The history image data may be stored as three-dimensional volume data and rendering image data.

The image database 19 may read image data stored in a storage medium such as an MO, CD-R, and DVD, and store the targeted image data.

The input interface circuitry 20 receives various instructions from the operator through the input device 60. The input device 60 may include a mouse, a keyboard, panel switches, slider switches, dial switches, a track ball, a rotary encoder, an operation panel, a touch command screen (TCS), and the like. The input device 60 includes mechanical switches 61 for performing the cropping operation onto the B-mode volume data and mechanical switches 62 for performing the cropping operation onto the blood flow volume data. The cropping operation is to edit volume data so as to visualize the inside of the volume data having a three-dimensional structure. The details of the cropping operation will be discussed later.

Both the switches 61 and the switches 62 include a start button to receive a start instruction for starting the cropping operation. The operator may press the start button included in the switches 61, and then set up a region of interest for the cropping operation of the B-mode volume data by manipulating the dial switch and/or track ball. The operator may also press the start button included in the switches 62, and then set up a region of interest for the cropping operation of the blood flow volume data by manipulating the dial switch and/or track ball.

According to the present embodiment, the operation for the B-mode volume data is performed by use of the switches 61, and the operation for the blood flow volume data is performed by use of the switches 62. However, the invention is not limited thereto. For example, by separating the timings of the cropping operation, the operations for both the B-mode volume data and blood flow volume data may be realized with a single set of switches.

The region of interest can be set, not only by the mechanical devices such as a dial switch and track ball, but by manipulating on an operation panel image displayed on the TCS or on an operation panel image displayed on the second console of the external device 40.

The input interface circuitry 20 may be connected to the control circuitry 22 via a bus so as to convert an operation instruction input by the operator to an electrical signal, and to output the electrical signal to the control circuitry 22. Throughout the specification, the input interface circuitry 20 should not be considered as being limited to a type that is connected to a physical operation component such as a mouse and keyboard. Examples of the input interface circuitry 20 may include an electrical signal processing circuit configured to receive, as a wireless signal, an electrical signal corresponding to the operation instruction that is input from an external input device provided separately from the ultrasound diagnostic apparatus 1 and to output this electrical signal to the control circuitry 22.

The communication interface circuitry 21 may be wirelessly connected to the position sensor system 30 to receive the positional information transmitted from the position detection device 32. The communication interface circuitry 21 is also connected to the external device 40 via a network 100 or the like, and performs data communications with the external device 40. The external device 40 may be a database of the picture archiving and communication system (PACS) that manages various types of medical image data, or a database of an electronic health record system that manages electronic charts to which medical images are attached. The external device 40 may be any medical image diagnostic apparatus other than the ultrasound diagnostic apparatus 1 according to the present embodiment, such as an x-ray CT apparatus, Magnetic Resonance Imaging (MRI) apparatus, nuclear medicine diagnostic apparatus, or x-ray diagnostic apparatus. Any communication standard may be adopted for communications with the external device 40, and one example may be DICOM.

The control circuitry 22 may be a processor that functions as the center of the ultrasound diagnostic apparatus 1. The control circuitry 22 implements the operation programs stored in the internal memory 17, and thereby realizes the functions corresponding to the operation programs. In particular, the control circuitry 22 is provided with a volume data acquiring function 221, ROI setting function 223, cropping function 225, display control function 227, and system control function 229.

The volume data acquiring function 221 is to acquire various types of volume data. When the volume data acquiring function 221 is implemented, the control circuitry 22 may control the ultrasound transmission circuitry 11, ultrasound reception circuitry 12, B-mode processing circuitry 13, Doppler processing circuitry 14, and 3D processing circuitry 15, and thereby acquire the B-mode volume data and/or blood flow volume data. The control circuitry 22 may read the volume data pre-stored in the image database 19 and thereby acquire the B-mode volume data and/or blood flow volume data.

The ROI setting function 223 is to set a region of interest (ROI) for various types of volume data acquired in accordance with the volume data acquiring function 221. When the ROI setting function 223 is implemented, the control circuitry 22 may set the ROI for the B-mode volume data and/or for the blood flow volume data based on the input information that is input by the operator through the input interface circuitry 20. The input information includes the position, angle, and dimensions (width, depth, height, etc.) of each volume data item. The input information may be preset.

The cropping function 225 is to perform the cropping operation onto the various volume data for which the ROI has been set up in accordance with the ROI setting function 223, and to generate display image data based on the volume data subjected to the cropping operation. When the cropping function 225 is implemented, the control circuitry 22 performs the cropping operation onto the B-mode volume data and/or blood flow volume data for which the ROI has been set. The cropping operation may be realized by setting the pixels of the cropping target volume data other than the ROI, to zero. Furthermore, the cropping operation may be realized by cutting the ROI that has been set, from the cropping target volume data. The cropping operation may be realized by setting the transparency of the ROI to 0% and the transparency of the area other than the ROI to 50% so that a difference is provided between the set ROI and the area other than the ROI in the transparency for the rendering operation. The control circuitry 22 generates the display image data based on the B-mode volume data and/or blood flow volume data after the cropping operation. The display image data includes rendering image data that represents a rendering image and MPR image data that represents an MPR image.

The display control function 227 is to display various types of volume data. When the display control function 227 is implemented, the control circuitry 22 displays the B-mode volume data and/or blood flow volume data acquired in accordance with the volume data acquiring function 221 on the display 50. The control circuitry 22 displays the display image data generated by the cropping function 225, on the display 50.

The system control function 229 is to control the basic operations of the ultrasound diagnostic apparatus 1 such as inputting and outputting. When the system control function 229 is implemented, the control circuitry 22 may receive the setting of the ROI of the volume data, for each of the volume data items, via the input interface circuitry 20. The control circuitry 22 may also receive the start of the cropping operation of the volume data, for each of the volume data items, via the input interface circuitry 20.

The volume data acquiring function 221, ROI setting function 223, cropping function 225, display control function 227, and system control function 229 may be incorporated into the control program. Alternatively, hardware circuits dedicated to implementing these functions may be incorporated within the control circuitry 22, or arranged in the apparatus main body 10 as circuits that can be referred to by the control circuitry 22.

Next, the ultrasound diagnostic apparatus 1 according to the present embodiment will be explained by referring to the flowchart of FIG. 2.

FIG. 2 is a flowchart of the operations of the control circuitry when the ultrasound diagnostic apparatus according to the present embodiment performs the cropping operation onto the volume data. In the following explanation, the regions of interest for the B-mode volume data and blood flow volume data are set by the operator through the input interface circuitry 20, and the cropping is performed in the order of the B-mode volume data and then the blood flow volume data. Alternatively, the cropping operation may be performed in the order of the blood flow volume data and then the B-mode volume data. The diagnosis target is the heart, and a matrix-transesophageal echocardiography (TEE) probe is employed as the ultrasound probe 70 for acquisition of the volume data. The regurgitation of the blood is to be checked at the aortic valve. Alternatively, a matrix-transthoracic echocardiography (TTE) probe may be adopted as the ultrasound probe 70. The targeted positions for checking the regurgitation of the blood may be at the mitral valve, tricuspid valve, or pulmonary valve. Furthermore, the diagnosis target may be any organ that contains blood vessels, such as a liver.

The control circuitry 22 implements the volume data acquiring function 221, responds to a specific instruction that is input from the operator through the input interface circuitry 20, and acquires the B-mode volume data and blood flow volume data of the heart that is the diagnosis target (step SA1). The control circuitry 22 may control the ultrasound transmission circuitry 11, ultrasound reception circuitry 12, B-mode processing circuitry 13, and 3D processing circuitry 15, and generate B-mode volume data based on the reflection wave signal received in real time from the ultrasound probe 70. The control circuitry 22 may further control the ultrasound transmission circuitry 11, ultrasound reception circuitry 12, Doppler processing circuitry 14, and 3D processing circuitry 15, and generate blood flow volume data based on the reflection wave signal received in real time from the ultrasound probe 70. In this manner, the B-mode volume data and blood flow volume data are acquired.

The control circuitry 22 implements the display control function 227 and generates the display image data based on the acquired B-mode volume data and blood flow volume data (step SA2). In particular, the control circuitry 22 may combine the B-mode volume data and blood flow volume data before the cropping operation, and thereby generate composite volume data. Thereafter, the control circuitry 22 performs the MPR process, rendering process, and the like onto the composite volume data, and thereby generates display image data.

Figure 3:
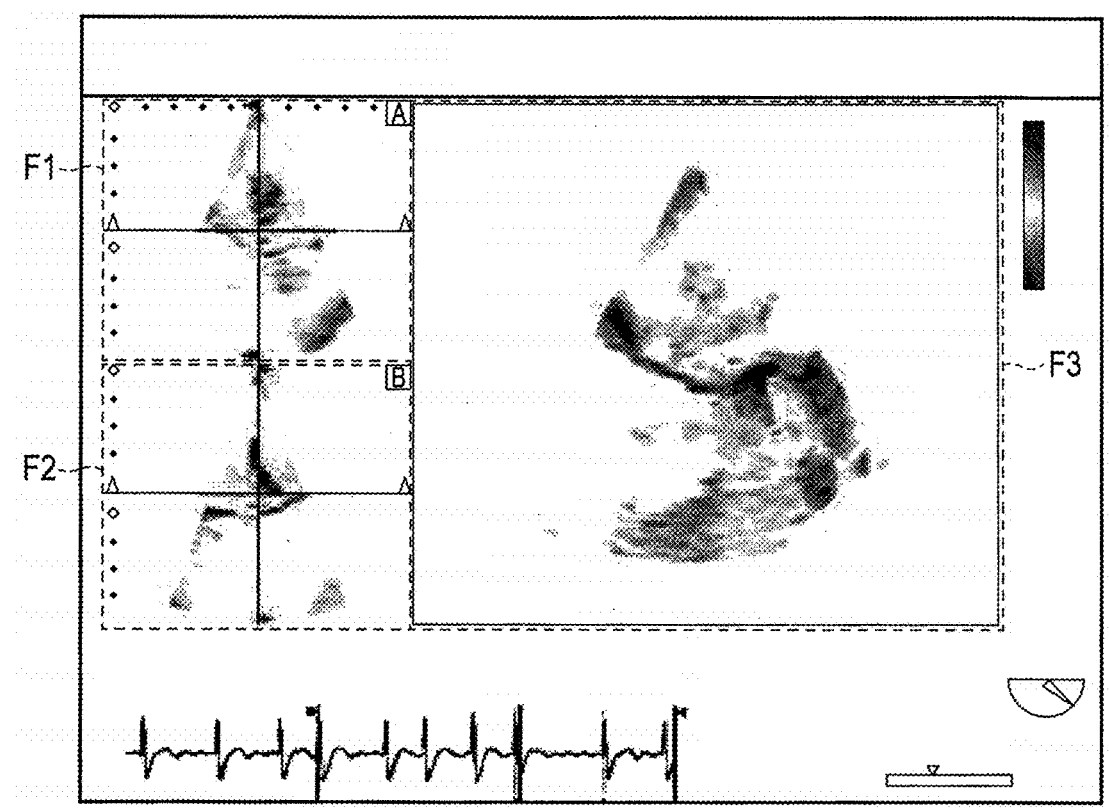
FIG. 3 is a diagram showing a display image before the cropping process, displayed on a display device according to the present embodiment.

The control circuitry 22 displays the generated display image data on the display 50 (step SA3). FIG. 3 is a diagram showing an example display image before the cropping operation, displayed on the display 50 according to the present embodiment. In the display area F1 of FIG. 3, an MPR image based on the region A of the MPR image data of the composite volume data before the cropping operation is displayed. The region A may be a cross section represented by the alignment direction of the piezoelectric transducers of the ultrasound probe 70 and the transmission direction of the ultrasonic beam. In the display area F2 of FIG. 3, an MPR image based on the region B of the MPR image data of the composite volume data before the cropping operation is displayed. The region B may be a cross section orthogonal to the contact surface of the ultrasound probe 70 and also orthogonal to the region A. The cross section orthogonal to the regions A and B, or in other words, the cross section vertical with respect to the transmission direction of the ultrasonic beam, is referred to as region C. The region C is a cross section parallel to the contact surface. The control circuitry 22 may superimpose the B-mode volume image based on the B-mode volume data before the cropping operation and the blood flow volume image based on the blood flow volume data before the cropping operation, and display the resultant image on the display 50.

In the display area F3 of FIG. 3, the rendering image based on the rendering image data before the cropping operation is displayed. Here, if the blood is flowing back at the cardiac valve of the subject P, the regurgitation cannot be clearly and visually identified on the display, with the blood flow volume data and B-mode volume data being superimposed with each other.

The control circuitry 22 implements the system control function 229, and receives the instruction for starting the cropping operation onto the B-mode volume data (step SA4). The instruction for starting the cropping operation onto the B-mode volume data may be received when the start button included in the switches 61 is pressed down. In order to identify which direction (view) of the heart the diagnosis target (heart) is observed from, a specific observation direction (line of vision and position of vision) may also be set via the input interface circuitry 20 in response to the start instruction.

When the start button included in the switches 61 is pressed down, the control circuitry 22 implements the ROI setting function 223, and thereby sets a region of interest for the B-mode volume data acquired at step SA1, in accordance with the input information designated by the operator via the input interface circuitry 20 (step SA5). The region of interest may be set by designating the depth of the B-mode volume data through the input interface circuitry 20. This depth represents the depth of the ultrasonic wave in the transmitting direction that is transmitted from the ultrasound probe 70, by referring to the position of the ultrasound probe 70 placed on the subject P during the ultrasonic imaging.

Specifically, the control circuitry 22 calculates the cropping surface which serves as the boundary surface that divides the cropping-target B-mode volume data, based on the designated depth of this volume data. The depth may be determined in accordance with the position of the aortic valve. The control circuitry 22 determines, as a region of interest, the spatial region included in the deeper side of the cropping-target volume data with respect to the calculated cropping surface. The cropping surface may be a cross section of the blood vessel that runs in the diagnosis-targeted heart in the shorter axis direction. The cropping surface may be a longitudinal cross section of the blood vessel that runs in the heart. The cropping surface is not limited to a planar surface, but may be a curved surface obtained, for example, from a "curved MPR" process. The ROI may be determined to be shaped into any polyhedron, or in a columnar, spherical, or oval form, depending on the operator's intended use. The information of the set ROI may be stored in the internal memory 17.

Figure 5:
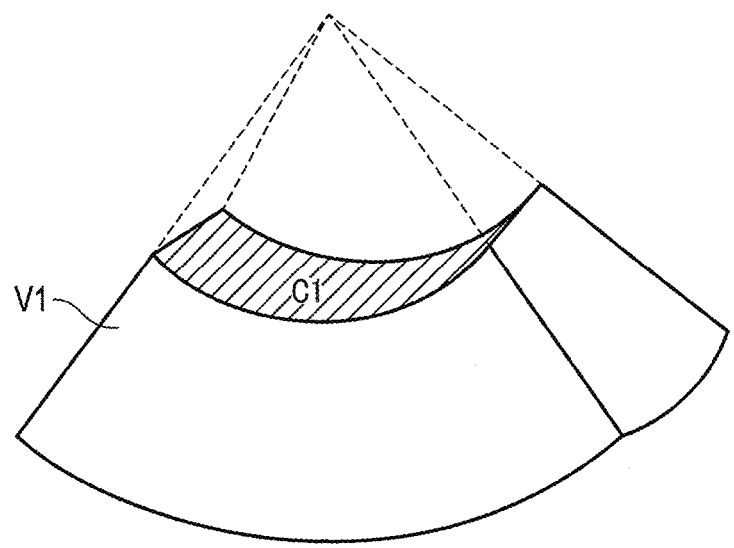
FIG. 5 is a schematic diagram for explaining the B-mode volume data that has been subjected to the cropping process according to the present embodiment.

When the region of interest is set for the B-mode volume data, the control circuitry 22 implements the cropping function 225 to perform the cropping operation onto the B-mode volume data for which the ROI has been set (step SA6). FIG. 5 is a schematic diagram for explaining the B-mode volume data subjected to the cropping operation according to the present embodiment. In FIG. 5, the solid-lined area is cut away along the boundary of the cropped surface C1, as B-mode volume data V1 after the cropping operation.

Figure 4:
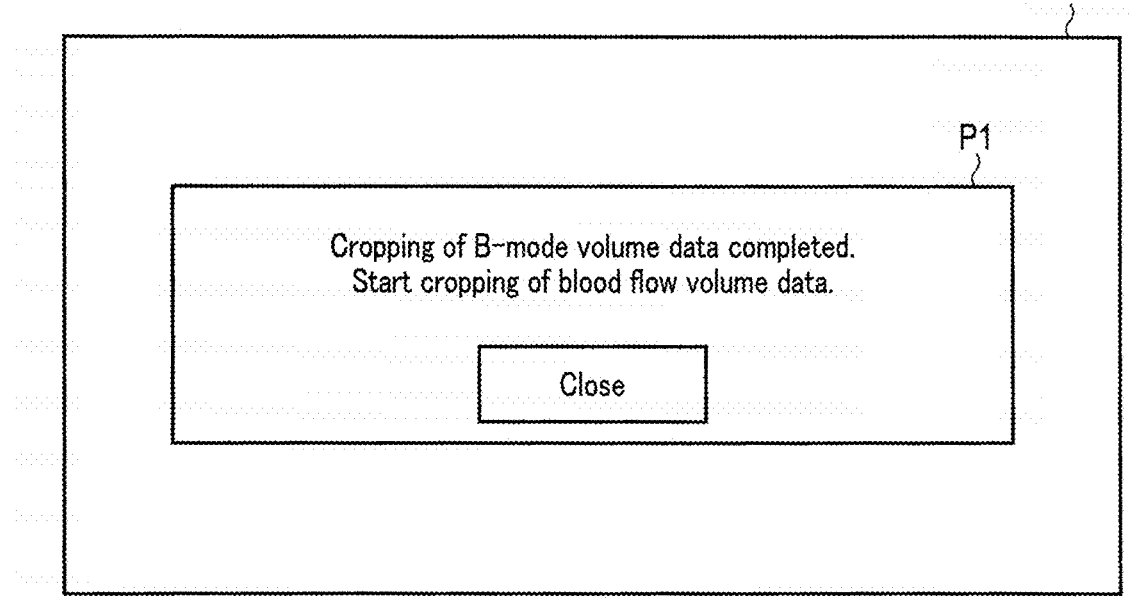
FIG. 4 is a diagram showing an example notification screen that prompts an operator to perform a cropping process onto blood flow volume data after the cropping process is performed onto B-mode volume data displayed on the display device according to the present embodiment.

After the cropping operation of the B-mode volume data is completed, the control circuitry 22 implements the system control function 229 to receive the instruction for starting the cropping operation on the blood flow volume data (step SA7). The instruction for starting the cropping operation on the blood flow volume data may be received when the start button included in the switches 62 is pressed. The control circuitry 22 may prompt the operator to start the cropping operation of the blood flow volume data, after the cropping operation is performed on the B-mode volume data. As the means for prompting the operator to start the cropping operation, a pop-up display may be employed. FIG. 4 is a diagram showing an example notification screen that prompts the operator to start the cropping operation on the blood flow volume data after the cropping operation is performed on the B-mode volume data displayed on the display 50 according to the present embodiment. A pop-up image P1 is displayed on the display 50 shown in FIG. 4. The pop-up image P1 may contain a character string "Cropping of B-mode volume data completed. Start cropping of blood flow volume data". In this manner, the operator can reliably conduct the cropping operation on the blood flow volume data. When a "close" button included in the pop-up image P1 is designated, the pop-up image P1 disappears.

When the start button included in the switches 62 is pressed, the control circuitry 22 may implement the ROI setting function 223, and set the region of interest for the blood flow volume data acquired at step SA1 in accordance with the input information designated by the operator through the input interface circuitry 20 (step SA8). The control circuitry 22 may set the ROI based on the pixel values assigned in accordance with the direction and velocity of the blood flow on the blood flow volume data. In particular, the control circuitry 22 detects a region in which the direction of the blood flow indicates a positive direction, or a region in which the direction of the blood flow indicates a negative direction, and sets the ROI based on the detected region. The positive direction of the blood flow may be the direction of flowing toward the ultrasound probe 70. The negative direction of the blood flow may be the direction of flowing away from the ultrasound probe 70.

The control circuitry 22 may set the region in which the direction of blood flow is negative, or in other words in which a regurgitation is caused, as the region of interest. The control circuitry 22 sets a predetermined threshold value for the pixel value of each voxel of the blood flow volume data, and thereby determines the size of the ROI. Here, the control circuitry 22 is configured to calculate the distance from the aortic valve to one end of the area of the blood regurgitation. This can reduce the variations in precision when determining the region of interest for the blood flow volume data, which tend to be caused by different operators' skills and experience. Furthermore, the operability can be improved during the 3D scanning and analyzing.

The threshold for determining the boundary between the cropping-target ROI and region other than the ROI may be set based on the maximum or minimum value of the velocity display scale, or the display range width, which is input through the input interface circuitry 20.

Furthermore, in accordance with the temporal phase of the end-diastole or any other temporal phase, the input information for the ROI of each volume data item may be adaptively changed. In this manner, a region resulting not from a blood stream but from any noise will not be displayed so that a component representing only the blood stream can be displayed.

The region of interest for the blood flow volume data may be set by designating the depth of the blood flow volume data through the input interface circuitry 20.

The information of the ROI that has been set may be stored in the internal memory 17.

Figure 6:
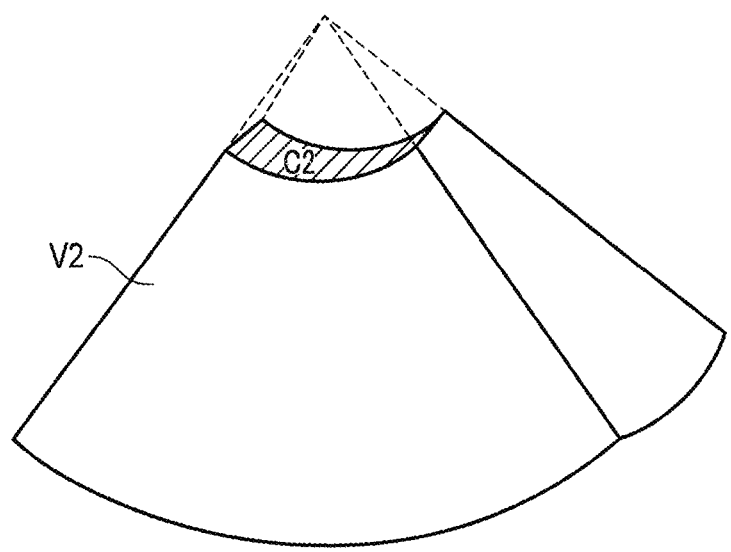
FIG. 6 is a schematic diagram for explaining the blood flow volume data that has been subjected to the cropping process according to the present embodiment.

When the region of interest is set for the blood flow volume data, the control circuitry 22 implements the cropping function 225 to perform the cropping operation onto the blood flow volume data, for which the region of interest has been set (step SA9). FIG. 6 is a schematic diagram for explaining an example of the blood flow volume data that has been subjected to the cropping according to the present embodiment. In FIG. 6, the solid-lined region is shown as blood flow volume data V2 that has been cut away after the cropping operation, with the cropped surface C2 serving as a boundary surface.

After performing the cropping operation on the blood flow volume data, the control circuitry 22 generates display image data, based on the B-mode volume data and blood flow volume data that have been subjected to the cropping (step SA10). In particular, the control circuitry 22 combines the B-mode volume data and blood flow volume data that have been subjected to the cropping, and generates the composite volume data.

Figure 7:
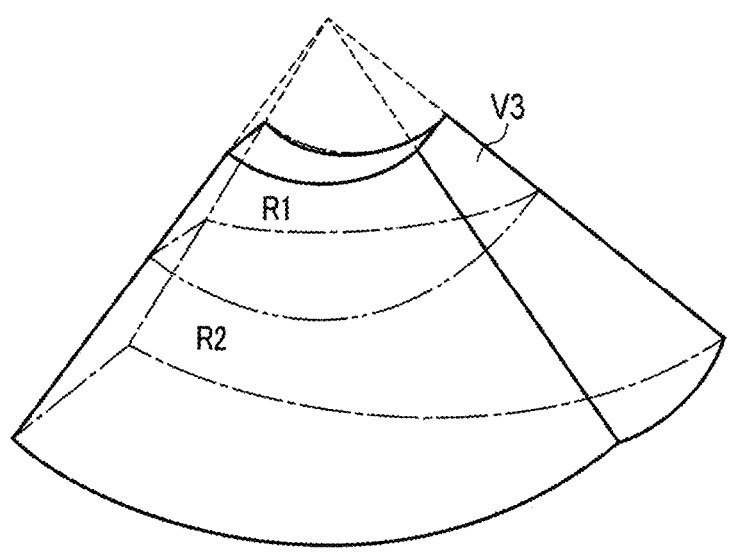
FIG. 7 is a schematic diagram explaining the composite volume data generated by the ultrasound diagnostic apparatus according to the present embodiment.

FIG. 7 is a schematic diagram explaining an example of the composite volume data generated by the ultrasound diagnostic apparatus according to the present embodiment. In FIG. 7, the composite volume data V3 generated based on the B-mode volume data V1 and blood flow volume data V2 which have been subjected to the cropping operation is illustrated in solid lines. Of the composite volume data V3, the space region R1 is a region in which only the blood flow volume data V2 is displayed. Of the composite volume data V3, the space region R1 is a region in which a regurgitation of blood may be caused if the aortic valve is not properly functioning. Of the composite volume data V3, the space region R2 is a region in which the B-mode volume data V1 and the blood flow volume data V2 are superimposed with each other.

The control circuitry 22 performs the MPR process and rendering process onto the generated composite volume data V3, and thereby generates the display image data.

Figure 8:
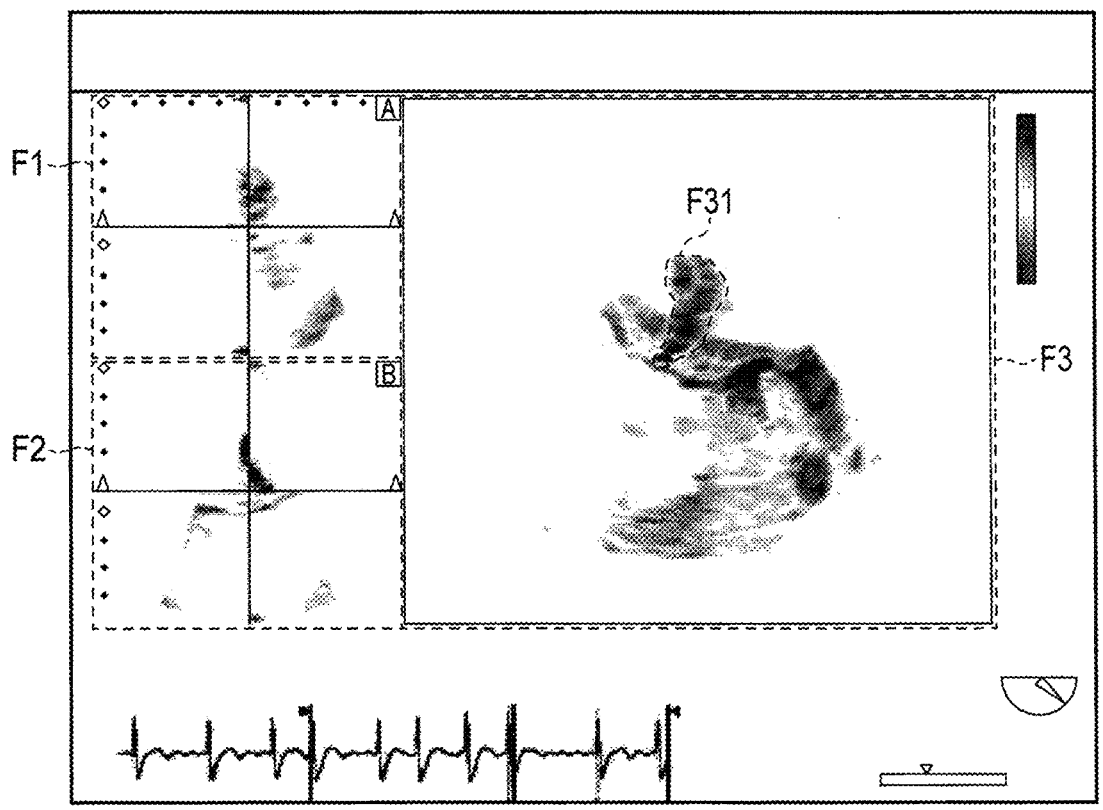
FIG. 8 is a diagram showing a display image subjected to the cropping process and displayed on the display device according to the present embodiment.

The control circuitry 22 displays a display image based on the generated display image data (step SA11). FIG. 8 is a diagram showing a display image after the cropping operation, displayed on the display 50 according to the present embodiment. The display area F1 in FIG. 8 shows an MPR image based on the region A of the MPR image data of the composite volume data after the cropping operation. The display area F2 in FIG. 8 shows an MPR image after the cropping based on the region B of the MPR image data of the composite volume data.

The display area F3 in FIG. 8 shows a rendering image based on the rendering image data after the cropping operation. The display area F31 in the display area F3 of FIG. 8 represents, for example, part of the region of the blood flow volume data approximately between the aortic valve and the apex cordis. In this display area F31, what is called a valve regurgitant jet flow has been caused. The display area F31 is three-dimensionally represented in the red hue (red to yellow). In the display area F31, the blood flowing through the aortic valve is flowing toward the ultrasound probe 70. The blood flowing through the aortic valve is supposed to flow from the apex cordis toward the aortic valve, and therefore the regurgitation of the blood around the aortic valve can be identified with the display of the display area F31. The display image displayed as in FIG. 8 allows for clear visual identification of the regurgitation of the blood at the cardiac valve, with the B-mode volume data removed.

The control circuitry 22 may superimpose and display, on the display 50, a B-mode volume image based on the B-mode volume data subjected to the cropping operation and a blood flow volume image based on the blood flow volume data subjected to the cropping operation.

According to the present embodiment, the control circuitry 22 acquires the B-mode volume data and the blood flow volume data. The control circuitry 22 sets the ROI independently for the B-mode volume data and the blood flow volume data. The control circuitry 22 performs the cropping operation onto the B-mode volume data, based on the information representing the ROI set for the B-mode volume data. The control circuitry 22 further performs the cropping operation on the blood flow volume data, based on the information representing the ROI set for the blood flow volume data. The control circuitry 22 generates a display image data, based on the B-mode volume data and blood flow volume data subjected to the cropping operation.

In this manner, when the B-mode volume data and blood flow volume data are superimposed with each other, the unnecessary region of the B-mode volume data that would interfere with the region relating to the blood flow volume data and indicating the regurgitation of the blood can be independently removed. As a result, the regurgitation of the blood at the cardiac valve can be observed.

Thus, the ultrasound diagnostic apparatus according to the present embodiment can facilitate the diagnosis of the blood flow at a cardiac test or the like.

OTHER MODIFICATION EXAMPLES

According to the above embodiment, any volume data other than the B-mode volume data has been dealt with as blood flow volume data, but the invention is not limited thereto. For example, to selectively display the harmonic components from the ultrasonic contrast agent, the volume data may be acquired by implementing the Contrast Harmonic Imaging (CHI).

According to the above embodiment, the control circuitry 22 independently performs the cropping operation onto two different types of volume data, namely the B-mode volume data and blood flow volume data, but the invention is not limited thereto. The control circuitry 22 may perform the cropping operation independently onto three or more different types of volume data.

Furthermore, according to the above embodiment, the cropping target of the control circuitry 22 is ultrasonic volume data acquired by the ultrasonic scanning such as B-mode volume data and blood flow volume data, but the invention is not limited thereto. The control circuitry 22 may perform the cropping operation on the volume data of medical image data acquired by another modality, such as CT image data, MR image data, x-ray image data, and PET image data. Here, if different types of volume data that are cropping targets are not imaged at the same timing, the control circuitry 22 first implements a certain registration processing onto these different types of volume data, and then performs the cropping process, independently onto the volume data of the different types.

Furthermore, the functions implemented by the control circuitry according to the present embodiment may be implemented by another modality, such as medical image diagnostic apparatuses including an x-ray CT apparatus, Magnetic Resonance Imaging (MRI) apparatus, nuclear medicinal diagnostic apparatus, and x-ray diagnostic apparatus.

The above embodiment has been explained based on the assumption that the invention is directed to an ultrasound diagnostic apparatus that is a medical image diagnostic apparatus, but the invention is not limited thereto. For example, different types of volume data acquired by various medical image diagnostic apparatuses may be transmitted to a personal computer (PC), a work station, and the like so as to implement the functions implemented by the control circuitry of the medical image processing apparatus according to the above embodiment.

According to the present embodiment, the control circuitry 22 detects a region indicating that the direction of the blood flow is positive, or a region indicating that the direction of the blood flow is negative, and sets the ROI for the blood flow volume data based on the detected region. However, the invention is not limited thereto. The control circuitry 22 may use an MPR image and automatically align the position of the ROI of the blood flow volume data to the MPR image. Alternatively, the control circuitry 22 may calculate a specific surface a certain distance away from a specific position, for example the position of the cardiac valve, in the B-mode volume data subjected to the cropping operation, and set the ROI for the blood flow volume data based on the calculated surface. Furthermore, the control circuitry 22 may extract the position of the cardiac valve from the B-mode volume data, and set, as a ROI, a region that extends from the extracted position of the valve to a position a certain distance away from this position of the valve.

The control circuitry 22 may set the ROI for the blood flow volume data, by using the apex cordis as a reference position. For example, the control circuitry 22 may multiply the distance from the center position of the cardiac valve annulus portion to the position of the apex cordis of the left ventricle with a specific rate, and thereby obtain the distance from the center position of the annulus portion to one end of the cropping target ROI. In this manner, the ROI data can be set for the blood flow volume.

The control circuitry 22 may set the ROI for various types of volume data, based on the setting information that has been preset regarding the ROI. The setting information may be pre-stored in the internal memory 17.

The control circuitry 22 may superimpose the blood flow volume data that has been subjected to the cropping operation onto the B-mode volume data that has not been subjected to the cropping operation to analyze the three-dimensional position of the cardiac valve, and thereby set the ROI for the B-mode volume data.

According to the above embodiment, the control circuitry 22 analyzes the blood flow volume data to set the ROI for the blood flow volume data, but the invention is not limited thereto. The control circuitry 22 may analyze the B-mode volume data to set the ROI for the blood flow volume data. Alternatively, the control circuitry 22 may analyze both the B-mode volume data and the blood flow volume data to set the ROI for the blood flow volume data.

According to the above embodiment, the instructions for starting the cropping operation of the B-mode volume data and the blood flow volume data are separately received, but the invention is not limited thereto. The control circuitry 22 may set the ROI for the blood flow volume data successively after the ROI is set for the B-mode volume data. The control circuitry 22 may perform the cropping operation on each of the B-mode volume data and the blood flow volume data, for which the ROI has been set.

In addition, according to the above embodiment, the control circuitry 22 superimposes the B-mode volume data and the blood flow volume data in the space region R2 of the composite volume data V3 illustrated in FIG. 7, but the invention is not limited thereto. The control circuitry 22 may extract only the B-mode volume data for the space region R2 illustrated in FIG. 7, and only the blood flow volume data for the space region R1.

According to the above embodiment, the control circuitry 22 may separately acquire two types of volume data, for example, B-mode volume data and blood flow volume data, and stores the acquired B-mode volume data and blood flow volume data separately in the internal memory 17, but the invention is not limited thereto. The control circuitry 22 may acquire one item of volume data including the B-mode data and Doppler data, and stores the acquired item of volume data in the internal memory 17. Here, the control circuitry 22 may implement the volume data acquiring function 221, and may acquire volume data related to the heart that is the diagnostic target, in response to the specific instruction from the operator through the input interface circuitry 20. This volume data may be based on the B-mode data related to a B-mode image and the Doppler data related to a color Doppler image. In particular, the control circuitry 22 may control the ultrasound transmission circuitry 11, the ultrasound reception circuitry 12, the B-mode processing circuitry 13, and the Doppler processing circuitry 14 to perform 3D B-mode scanning and 3D Doppler scanning in combination. The B-mode data and Doppler data is generated based on the reflection wave signals received in real time via the ultrasound probe 70. The control circuitry 22 may control the 3D processing circuitry 15, and may generate the volume data based on the generated B-mode data and Doppler data. In this manner, the volume data item is acquired based on the B-mode data and Doppler data. The control circuitry 22 may then store the volume data item in the internal memory 17.

Thereafter, the control circuitry 22 sets the first region of interest for the first data included in the volume data, and sets the second region of interest for the second data that is included in the volume data and different from the first data. The first data may be based on the B-mode data. The second data may be based on the Doppler data. The control circuitry 22 performs the cropping operation on the first data and second data, based on the information representing the set first region of interest and second region of interest. The control circuitry 22 generates display image data based on the first data and second data that have been subjected to the cropping operation.

The term "processor" used in the above description may denote a Central Processing Unit (CPU), Graphics Processing Unit (GPU), or any circuitry such as an Application Specific Integrated Circuit (ASIC) and Programmable Logic Device (e.g., Simple Programmable Logic Device (SPLD), Complex Programmable Logic Device (CPLD), and Field Programmable Gate Array (FPGA)). The processor realizes the functions by reading and executing the programs stored in the memory circuitry. The processors of the above embodiment do not have to be each configured as a single circuit, but may be a single processor by combining a plurality of independent circuits to implement their functions. Furthermore, the structural elements in FIG. 1 may be integrated into one processor to implement their functions.

Several embodiments of the present invention have been explained, merely as examples, and thus are not meant to restrict the scope of invention. These novel embodiments may be realized in various other forms, and omission, replacement and modification may be freely made without departing from the gist of the invention. The accompanying claims and their equivalents are intended to cover such forms or modifications and would fall within the scope and spirit of the invention.

The invention claimed is:

1. A medical image diagnostic apparatus comprising processing circuitry configured to:
   acquire first volume data and second volume data relating to a subject;
   set a first region of interest for the first volume data, and set a second region of interest for the second volume data independently from setting of the first region of interest;
   perform a cropping process on the first volume data and the second volume data based on information representing the first region of interest and the second region of interest; and
   generate display image data based on the first volume data and the second volume data that have been subjected to the cropping process,
   wherein the first volume data is B-mode volume data of a B-mode image, and the second volume data is blood flow volume data of a Doppler image.

2. The medical image diagnostic apparatus according to claim 1, wherein the processing circuitry is configured to set the second region of interest based on analysis of at least either one of the first volume data and the second volume data.

3. The medical image diagnostic apparatus according to claim 1, wherein the first volume data and the second volume data are ultrasonic volume data collected by ultrasonic scanning, and the processing circuitry is configured to set the first region of interest and the second region of interest by designating a depth for each of the first volume data and the second volume data.

4. The medical image diagnostic apparatus according to claim 1, wherein the processing circuitry is configured to generate third volume data by combining the first volume data and the second volume data that have been subjected to the cropping process, and to generate the display image data by performing a rendering process onto the third volume data.

5. The medical image diagnostic apparatus according to claim 1, wherein the processing circuitry is configured to set the second region of interest by referring to a specific position of the subject.

6. The medical image diagnostic apparatus according to claim 1, wherein the cropping process is at least either one of a process in which pixel values in a region other than the first region of interest are set to zero and a process in which pixel values in a region other than the second region of interest are set to zero.

7. The medical image diagnostic apparatus according to claim 1, wherein in the cropping process, the first region of interest and/or the second region of interest are cut away from volume data targeted for the cropping process.

8. The medical image diagnostic apparatus according to claim 1, wherein in the cropping process, a difference is provided between transparency in the first region of interest and transparency in a region other than the first region of interest for a rendering process and/or between transparency in the second region of interest and transparency in a region other than the second region of interest for the rendering process.

9. The medical image diagnostic apparatus according to claim 1, wherein the processing circuitry is configured to provide, after performing the cropping process onto the first volume data, a prompt for performing the cropping process onto the second volume data.

10. A medical image diagnostic apparatus comprising processing circuitry configured to:
    acquire volume data including first data, second data and third data relating to a subject, the first, second and third data each being volume data and each being different from each other;
    set a first region of interest for the first data, set a second region of interest for the second data, and set a third region of interest for third data;
    perform a cropping process onto the first data, the second data, and the third data based on information representing the first region of interest, the second region of interest and the third region of interest; and generate display image data based on the first data, the second data and the third data that have been subjected to the cropping process.

11. The medical image diagnostic apparatus according to claim 10, wherein the volume data is ultrasonic volume data collected by ultrasonic scanning, and the processing circuitry is configured to set the first region of interest and the second region of interest by designating a depth for each of the first data and the second data.

12. The medical image diagnostic apparatus according to claim 10, wherein the first data is B-mode data of a B-mode image, and the second data is blood flow data of a color Doppler image.

13. The medical image diagnostic apparatus according to claim 10, wherein the processing circuitry is configured to set the second region of interest by referring to a specific position of the subject.

14. The medical image diagnostic apparatus according to claim 10, wherein the cropping process is at least either one of a process in which pixel values in a region other than the first region of interest are set to zero and a process in which pixel values in a region other than the second region of interest are set to zero.

15. The medical image diagnostic apparatus according to claim 10, wherein in the cropping process, the first region of interest and/or the second region of interest are cut away from the volume data.

16. The medical image diagnostic apparatus according to claim 10, wherein in the cropping process, a difference is provided between transparency in the first region of interest and transparency in a region other than the first region of interest for a rendering process and/or between transparency in the second region of interest and transparency in a region other than the second region of interest for the rendering process.

17. The medical image diagnostic apparatus according to claim 10, wherein the processing circuitry is further configured to provide, after performing the cropping process onto the first data, a prompt for performing the cropping process onto the second data.

18. A medical image processing apparatus, comprising processing circuitry configured to:
  acquire first volume data including B-mode data and second volume data including Doppler data relating to a subject;
  set a first region of interest for the first volume data, and set a second region of interest for the second volume data independently from setting of the first region of interest;
  perform a cropping process on the first volume data and the second volume data based on information representing the first region of interest and the second region of interest; and
  generate display image data based on the first volume data and the second volume data that have been subjected to the cropping process.

19. A medical image processing apparatus, comprising processing circuitry configured to:
  acquire volume data including B-mode data and Doppler data relating to a subject;
  set a first region of interest for the B-mode data included in the volume data, and set a second region of interest for the Doppler data that is included in the volume data;
  perform a cropping process onto the B-mode data and the Doppler data based on information representing the first region of interest and the second region of interest; and
  generate display image data based on the B-mode data and the Doppler data that have been subjected to the cropping process.

20. A medical image processing method comprising:
  acquiring first volume data and second volume data relating to a subject, the first volume data derived from medical image data acquired by a first imaging modality and the second volume data being derived from medical image data acquired by a second imaging modality different from the first imaging modality;
  setting a first region of interest for the first volume data, and a second region of interest for the second volume data independently from setting of the first region of interest;
  performing a cropping process on the first volume data and the second volume data based on information representing the first region of interest and the second region of interest; and
  generating display image data based on the first volume data and the second volume data that have been subjected to the cropping process.

21. A medical image processing method, comprising:
  acquiring volume data including B-mode data and Doppler data relating to a subject;
  setting a first region of interest for the B-mode data included in the volume data, and setting a second region of interest for the Doppler data that is included in the volume data
  performing a cropping process onto the B-mode data and the Doppler data based on information representing the B-mode region of interest and the second region of interest; and
  generating display image data based on the first data and the Doppler data that have been subjected to the cropping process.

22. The medical image diagnostic apparatus according to claim 1, wherein
  the first volume data subjected to the cropping process and the second volume data subjected to the cropping process respectively have regions that at least partially overlap each other.

* * * * *